US00PP18000P2

(12) United States Plant Patent
Meulenbroek

(10) Patent No.: US PP18,000 P2
(45) Date of Patent: Sep. 11, 2007

(54) STRAWBERRY PLANT NAMED 'SONATA'

(50) Latin Name: *Fragaria L.*
Varietal Denomination: Sonata

(75) Inventor: Egbertus Joseph Meulenbroek, Zetten (NL)

(73) Assignee: Plant Research International B.V., Wageningen (NL)

( * ) Notice: Subject to any disclaimer, the term of this patent is extended or adjusted under 35 U.S.C. 154(b) by 31 days.

(21) Appl. No.: 11/188,967

(22) Filed: Jul. 25, 2005

(51) Int. Cl.
*A01H 5/00* (2006.01)

(52) U.S. Cl. ..... Plt./208
(58) Field of Classification Search ..... Plt./208
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of Strawberry plant named 'Sonata', characterized by its compact growth habit; large and uniformly conical fruits; firm fruits; glossy light red-colored fruits; and pleasant fruit aroma and taste.

2 Drawing Sheets

Botanical designation: *Fragaria L.*
Cultivar denomination: 'Sonata'.

BACKGROUND OF THE INVENTION

The present Invention relates to a new and distinct cultivar of Strawberry plant, botanically known as *Fragaria L.*, and hereinafter referred to by the name 'Sonata'.

The new Strawberry is a product of a planned breeding program conducted by the Inventor in Wageningen, The Netherlands. The objective of the breeding program was to develop new high-yielding Strawberry cultivars with good fruit quality, good postharvest longevity and ease of harvesting.

The new Strawberry originated from a cross-pollination made by the Inventor during the summer of 1990 of the *Fragaria L.* cultivar Elsanta, not patented, as the female, or seed, parent with the *Fragaria L.* cultivar Polka, not patented, as the male, or pollen, parent. The new Strawberry was discovered and selected by the Inventor from within the resultant progeny from the above-mentioned cross-pollination in a controlled environment in Wageningen, The Netherlands during the summer of 1992.

Asexual reproduction since the fall of 1992 of the new cultivar by cuttings in a controlled environment in Elst, The Netherlands, has shown that the unique features of this new Strawberry are stable and reproduced true to type in successive generations.

SUMMARY OF THE INVENTION

The following traits have been repeatedly observed and are determined to be the unique characteristics of 'Sonata'. These characteristics in combination distinguish 'Sonata' as a new and distinct cultivar:

1. Compact growth habit.
2. Large and uniformly conical fruits.
3. Firm fruits.
4. Glossy light red-colored fruits.
5. Pleasant fruit aroma and taste.

Plants of the new Strawberry can be compared to plants of the female parent, the cultivar Elsanta. Plants of the new Strawberry differ from plants of the cultivar Elsanta in the following characteristics:

1. Plants of the new Strawberry are more compact than plants of the cultivar Elsanta.
2. Plants of the new Strawberry have smaller flowers than plants of the cultivar Elsanta.
3. Fruits of plants of the new Strawberry are shorter than fruits of plants of the cultivar Elsanta.
4. Fruits of plants of the new Strawberry are light red in color whereas fruits of plants of the cultivar Elsanta are brownish red in color.

Plants of the new Strawberry can be compared to plants of the male parent, the cultivar Polka. Plants of the new Strawberry differ from plants of the cultivar Polka in the following characteristics:

1. Plants of the new Strawberry are more compact than and not as vigorous as plants of the cultivar Polka.
2. Leaves of plants of the new Strawberry are not as rounded as leaves of plants of the cultivar Polka.
3. Fruits of plants of the new Strawberry are larger than fruits of plants of the cultivar Polka.
4. Fruits of plants of the new Strawberry are glossier and lighter red in color than fruits of plants of the cultivar Polka.

Plants of the cultivar Sonata can be compared to the cultivar Gorella, not patented. However, in side-by-side comparisons conducted in Wageningen, The Netherlands, plants of the new Strawberry and the cultivar Gorella differed in the following characteristics:

1. Plants of the new Strawberry were more compact than plants of the cultivar Gorella.
2. Fruits of plants of the new Strawberry were more uniform in shape than fruits of plants of the cultivar Gorella.
3. Fruits of plants of the new Strawberry were glossier than fruits of plants of the cultivar Gorella.
4. Fruits of plants of the new Strawberry were light red in color whereas fruits of plants of the cultivar Gorella were brownish red in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description, which accurately describe the actual colors of the new Strawberry.

The photograph on the first sheet comprises a side view of typical plants of 'Sonata' grown in an outdoor nursery.

The photograph on the second sheet is a close-up view of typical fruits of 'Sonata'.

DETAILED BOTANICAL DESCRIPTION

Plants of the cultivar Sonata have not been observed under all possible environmental conditions. The phenotype may vary somewhat with variations in environment such as temperature, light intensity and daylength without, however, any variance in genotype.

In the following description, color references are made to The Royal Horticultural Society Colour Chart, 2001 Edition, except where general terms of ordinary dictionary significance are used. Plants used for the aforementioned photograph and following description were grown in an outdoor nursery under conditions that closely approximate commercial production conditions during the spring and summer in Wageningen, The Netherlands. During the production of the plants, day temperatures ranged from 12° C. to 30° C. and night temperatures ranged from 5° C. to 20° C. Plants were about one year old when the photograph and description were taken.

Botanical classification: *Fragaria L.* cultivar Sonata.

Parentage:

*Female parent.*—*Fragaria L.* cultivar Elsanta, not patented.

*Male parent.*—*Fragaria L.* cultivar Polka, not patented.

Propagation:

*Type.*—By cuttings.

*Root description.*—Fine, fibrous and well branched; light brown in color.

Plant description:

*Plant form/habit.*—Upright and open plant habit. Plants flattened globose in form. Leaves basal, dense and bushy plant habit. Compact growth habit; moderately rapid growth rate. Many crowns per plant.

*Plant height.*—About 20 to 25 cm.

*Plant diameter.*—About 30 to 35 cm.

*Foliage description.*—Arrangement: Basal rosette; compound with typically three leaflets. Length: About 6 to 9 cm. Width: About 5 to 8 cm. Shape: Broadly ovate. Apex: Obtuse. Base: Obtuse to rounded. Margin: Serrate. Texture, upper and lower surfaces: Pubescent. Venation: Pinnate. Color: Developing foliage, upper surface: 137A. Developing foliage, lower surface: 138A. Fully developed foliage, upper surface: 137A to 139A; venation, 137A. Fully developed foliage, lower surface: Close to 137B; venation, 144C. Petiole length: About 9 to 13 cm. Petiole diameter: About 2 to 3 mm. Petiole color, upper and lower surfaces: 145A.

Flower description:

*Flower type and habit.*—Rotate flowers arranged singly at lateral apices. Flowers held at or above the leaf canopy. Flowers not fragrant.

*Natural flowering season.*—Early flowering; plants begin flower late April to early May in The Netherlands.

*Flower size.*—Diameter: About 3 to 3.5 cm. Depth (height): About 5 mm.

*Petals.*—Arrangement: Single whorl of about six petals, imbricate. Length: About 1.5 cm. Width: About 1.5 cm. Shape: Broadly ovate. Apex: Rounded. Base: Attenuate. Margin: Entire. Texture, upper and lower surfaces: Smooth, glabrous; satiny. Color: When opening and fully opened, upper surface: 155D. When opening and fully opened, lower surface: 155D.

*Sepals.*—Arrangement: Single whorl of 10 to 12 sepals, star-shaped calyx; calyx situated in a basin; attitude of the calyx segments is spreading and similar in size as the fruit diameter. Adherence of the calyx is weak to medium. Length: About 1.5 cm. Width: About 5 mm. Shape: Lanceolate. Apex: Acute. Base: Fused. Margin: Entire. Texture, upper and lower surfaces: Pubescent. Color, upper and lower surfaces: Close to 137A.

*Peduncles.*—Length: About 7 to 10 cm. Diameter: About 1 to 2 mm. Strength: Strong. Color: 144B.

*Reproductive organs.*—Stamens: Quantity per flower: About 25. Anther length: About 2 mm. Anther color: 14B. Pollen amount: Abundant. Pollen color: 15C. Pistils: Quantity per flower: About 30. Stigma shape: Rounded. Stigma color: Close to 5A. Fruits: Time of fruiting: During June in The Netherlands. Keeping quality: About five to ten days. Length: About 4 to 5 cm. Diameter: About 5 to 6 cm. Shape: Rounded conical; uniform. Truss length: Relatively short; flowers above the foliage. Hollow center size: Absent or weakly expressed. Firmness: Moderately firm. Fragrance, taste: Sweet, pleasant. Luster: Glossy. Color: 33A. Flesh color: Close to 33A. Achene insertion: Level with the fruit surface. Achene color: 1A; on shoulders of the fruit when exposed to light, 33A.

Disease/pest resistance: Plants of the new Strawberry have not been noted to be resistant to pathogens and pests common to Strawberry.

Temperature tolerance: Plants of the new Strawberry have been observed to tolerate temperatures ranging from 0° C. to 35° C.

It is claimed:

1. A new and distinct cultivar of Strawberry plant named 'Sonata', as illustrated and described.

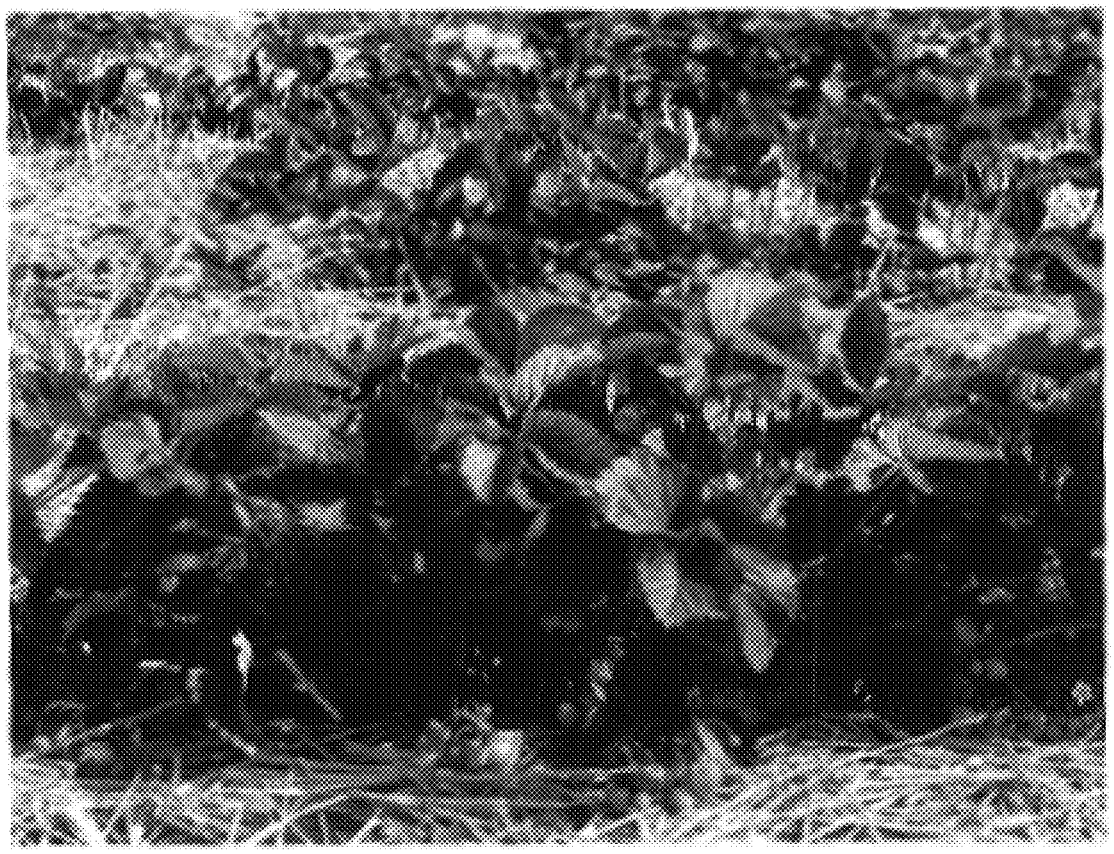

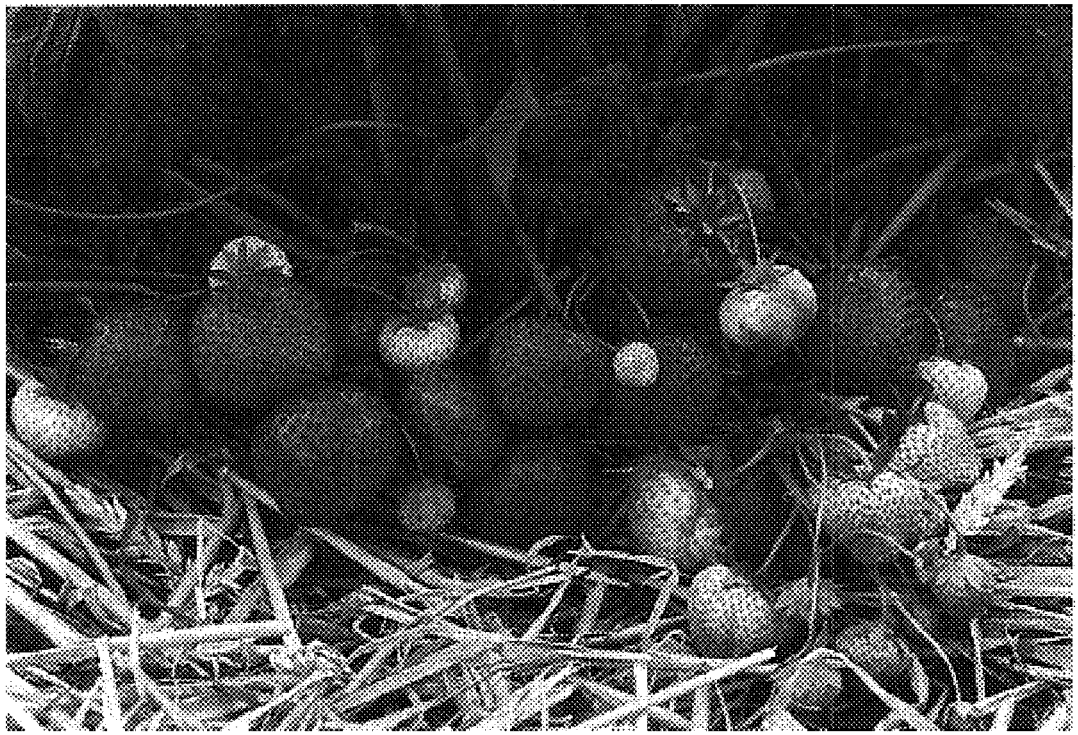

* * * * *